US007270705B2

(12) United States Patent
Lin et al.

(10) Patent No.: US 7,270,705 B2
(45) Date of Patent: *Sep. 18, 2007

(54) METHOD OF INCREASING WORKING TIME OF TETRACALCIUM PHOSPHATE CEMENT PASTE

(76) Inventors: Jiin-Huey Chern Lin, 911 Tower Rd., Winnetka, IL (US) 60093; Chien-Ping Ju, 62901, Carbondale, IL (US) 62901; Wen-Cheng Chen, No. 12, Bau-Shing St., Gueiren Shiang (TW); Kuan-Liang Lin, No. 27, Lane 69 Shian St., Fengyuan (TW); I-Chang Wang, No. 114, Jinhu Tsuen, Beimen Shiang (TW)

( * ) Notice: Subject to any disclaimer, the term of this patent is extended or adjusted under 35 U.S.C. 154(b) by 271 days.

This patent is subject to a terminal disclaimer.

(21) Appl. No.: 10/940,922

(22) Filed: Sep. 14, 2004

(65) Prior Publication Data
US 2005/0069479 A1 Mar. 31, 2005

Related U.S. Application Data

(63) Continuation-in-part of application No. 10/773,701, filed on Feb. 6, 2004, which is a continuation-in-part of application No. 10/607,023, filed on Jun. 27, 2003, now Pat. No. 6,960,249, which is a continuation-in-part of application No. 10/414,582, filed on Apr. 16, 2003, now Pat. No. 7,094,282, which is a continuation-in-part of application No. 09/615,384, filed on Jul. 13, 2000, now abandoned, which is a continuation-in-part of application No. 09/351,912, filed on Jul. 14, 1999, now Pat. No. 6,379,453.

(51) Int. Cl.
C04B 12/02 (2006.01)
(52) U.S. Cl. ...................... 106/690; 106/691
(58) Field of Classification Search ............... 106/690, 106/691
See application file for complete search history.

(56) References Cited

U.S. PATENT DOCUMENTS

| 3,679,360 | A | 7/1972 | Rubin et al. |
| 4,371,484 | A | 2/1983 | Inukai et al. |
| 4,481,175 | A | 11/1984 | Iino et al. |
| 4,518,430 | A | 5/1985 | Brown et al. |
| 4,553,272 | A | 11/1985 | Mears |
| 4,612,053 | A | 9/1986 | Brown et al. |
| 4,623,553 | A | 11/1986 | Ries et al. |
| RE33,161 | E | 2/1990 | Brown et al. |
| RE33,221 | E | 5/1990 | Brown et al. |
| 4,959,104 | A | 9/1990 | Iino et al. |
| 5,017,518 | A | 5/1991 | Hirayama et al. |
| 5,053,212 | A | 10/1991 | Constantz et al. |
| 5,092,888 | A | 3/1992 | Iwamoto et al. |
| 5,149,368 | A | 9/1992 | Liu et al. |
| 5,152,791 | A | 10/1992 | Hakamatsuka et al. |
| 5,164,187 | A | 11/1992 | Constantz et al. |
| 5,180,426 | A | 1/1993 | Sumita |
| 5,218,035 | A | 6/1993 | Liu |
| 5,262,166 | A | 11/1993 | Liu et al. |
| 5,336,264 | A | 8/1994 | Constantz et al. |
| 5,338,356 | A | 8/1994 | Hirano et al. |
| 5,342,441 | A | 8/1994 | Mandai et al. |
| 5,409,982 | A | 4/1995 | Imura et al. |
| 5,476,647 | A | 12/1995 | Chow et al. |
| 5,492,768 | A | 2/1996 | Okimatsu et al. |
| 5,496,399 | A | 3/1996 | Ison et al. |
| 5,503,164 | A | 4/1996 | Friedman |
| 5,522,893 | A | 6/1996 | Chow et al. |
| 5,525,148 | A | 6/1996 | Chow et al. |
| 5,536,575 | A | 7/1996 | Imura et al. |
| 5,542,973 | A | 8/1996 | Chow et al. |
| 5,545,254 | A | 8/1996 | Chow et al. |
| 5,550,172 | A | 8/1996 | Regula et al. |
| 5,569,490 | A | 10/1996 | Imura et al. |
| 5,605,713 | A | 2/1997 | Boltong |
| 5,607,685 | A | 3/1997 | Cimbollek et al. |
| 5,652,016 | A | 7/1997 | Shiro et al. |
| 5,683,461 | A | 11/1997 | Lee et al. |
| 5,683,496 | A | 11/1997 | Ison et al. |
| 5,695,729 | A | 12/1997 | Chow et al. |
| 5,697,981 | A | 12/1997 | Ison et al. |

(Continued)

FOREIGN PATENT DOCUMENTS

| EP | 0267624 | | 5/1988 |
| EP | 1172076 | * | 7/2002 |
| JP | 06-228011 | | 8/1994 |
| WO | WO 03/055418 | | 7/2003 |

OTHER PUBLICATIONS

Pickel et al., "The Effect of a Chewing Gum Containing Dicalcium Phosphate on Salivary Calcium and Phosphate", Ala. J. Med. Sci. 1965, vol. 2, pp. 286-287.
Matsuya et al., "Effects of pH on the Reactions of Tetracalcium Phosphate and Dicalcium Phosphate", IADR Abstract 1991.
Sugawara et al,, "Formation of Hydroxyapatite in Hydrogels from Tetracalcium Phosphate/Dicalcium Phosphate Mixtures," J. Nihon. Univ. Sch. Dent., 1989, vol. 31, pp. 372-381.
Hong et al., The Periapical Tissue Reactions to a Calcium Phosphate Cement in the Teeth of Monkeys, J Biomed Mater Res. Apr. 1991, vol. 25(4), pp. 485-498.
Gburek et al., "Mechanical Activation of Tetracalcium Phosphate," J. Am. Ceram. Soc., vol. 87(2), pp. 311-313, 2004.

*Primary Examiner*—C. Melissa Koslow
(74) *Attorney, Agent, or Firm*—Meyertons, Hood, Kivlin, Kowert & Goetzel, P.C.; Eric B. Meyertons

(57) ABSTRACT

A method for increasing working time/setting time of monolithic tetracalcium phosphate (TTCP) cement paste formed by mixing a TTCP powder with an aqueous solution, which includes heating the TTCP powder, prior to the mixing, so that the TTCP powder is maintained at a temperature of 50-350° C. for a period of time which is greater than one minute, and that a TTCP cement paste formed by mixing the resulting heated TTCP powder with the aqueous solution has a prolonged working time in comparison with that formed by mixing TTCP powder that has not been subjected to such heating with the aqueous solution.

25 Claims, No Drawings

U.S. PATENT DOCUMENTS

| | | |
|---|---|---|
| 5,702,449 A | 12/1997 | McKay |
| 5,766,669 A | 6/1998 | Pugh et al. |
| 5,782,971 A | 7/1998 | Constantz et al. |
| 5,814,681 A | 9/1998 | Hino et al. |
| 5,820,632 A | 10/1998 | Constantz et al. |
| 5,846,312 A | 12/1998 | Ison et al. |
| 5,891,448 A | 4/1999 | Chow et al. |
| 5,899,939 A | 5/1999 | Boyce et al. |
| 5,954,867 A | 9/1999 | Chow et al. |
| 5,958,430 A | 9/1999 | Campbell et al. |
| 5,964,932 A | 10/1999 | Ison et al. |
| 5,976,234 A | 11/1999 | Chow et al. |
| 5,993,535 A | 11/1999 | Sawamura et al. |
| 5,997,624 A | 12/1999 | Chow et al. |
| 6,005,162 A | 12/1999 | Constantz |
| 6,013,591 A | 1/2000 | Ying et al. |
| 6,013,853 A | 1/2000 | Athanasiou et al. |
| 6,018,095 A | 1/2000 | Lerch et al. |
| 6,027,742 A | 2/2000 | Lee et al. |
| 6,077,989 A | 6/2000 | Kandel et al. |
| 6,083,229 A | 7/2000 | Constantz et al. |
| 6,117,456 A | 9/2000 | Lee et al. |
| 6,118,043 A | 9/2000 | Nies et al. |
| 6,123,731 A | 9/2000 | Boyce et al. |
| 6,132,463 A | 10/2000 | Lee et al. |
| 6,149,688 A | 11/2000 | Brosnahan et al. |
| 6,162,258 A | 12/2000 | Scarborough et al. |
| 6,277,149 B1 | 8/2001 | Boyle et al. |
| 6,294,041 B1 | 9/2001 | Boyce et al. |
| 6,294,187 B1 | 9/2001 | Boyce et al. |
| 6,323,146 B1 | 11/2001 | Pugh et al. |
| 6,325,987 B1 | 12/2001 | Sapieszko et al. |
| 6,325,992 B1 | 12/2001 | Chow et al. |
| 6,332,779 B1 | 12/2001 | Boyce et al. |
| 6,340,648 B1 | 1/2002 | Imura et al. |
| 6,379,453 B1 | 4/2002 | Lin et al. |
| 6,440,444 B2 | 8/2002 | Boyce et al. |
| 6,458,162 B1 | 10/2002 | Koblish et al. |
| 6,478,825 B1 | 11/2002 | Winterbottom et al. |
| 6,495,156 B2 | 12/2002 | Wenz et al. |
| 6,530,955 B2 | 3/2003 | Boyle et al. |
| 6,533,821 B1 | 3/2003 | Lally |
| 6,547,866 B1 | 4/2003 | Edwards et al. |
| 6,569,489 B1 | 5/2003 | Li |
| 6,585,992 B2 | 7/2003 | Pugh et al. |
| 6,616,742 B2 | 9/2003 | Lin et al. |
| 6,648,960 B1 * | 11/2003 | Lin et al. ............ 106/690 |
| 6,670,293 B2 | 12/2003 | Edwards et al. |
| 6,696,073 B2 | 2/2004 | Boyce et al. |
| 6,719,989 B1 | 4/2004 | Matsushima et al. |
| 6,730,129 B1 | 5/2004 | Hall et al. |
| 6,752,831 B2 | 6/2004 | Sybert et al. |
| 6,793,725 B2 | 9/2004 | Chow et al. |
| 6,808,561 B2 | 10/2004 | Genge et al. |
| 6,808,585 B2 | 10/2004 | Boyce et al. |
| 6,840,995 B2 | 1/2005 | Lin et al. |
| 6,929,692 B2 | 8/2005 | Tas |
| 6,953,594 B2 | 10/2005 | Lee et al. |
| 6,955,716 B2 | 10/2005 | Xu et al. |
| 6,960,249 B2 | 11/2005 | Lin et al. |
| 2002/0019635 A1 | 2/2002 | Wenstrom, Jr. et al. |
| 2002/0073894 A1 | 6/2002 | Genge et al. |
| 2002/0137812 A1 | 9/2002 | Chow et al. |
| 2003/0019396 A1 | 1/2003 | Edwards et al. |
| 2003/0031698 A1 | 2/2003 | Roeder et al. |
| 2003/0039676 A1 | 2/2003 | Boyce et al. |
| 2003/0055512 A1 | 3/2003 | Genin et al. |
| 2003/0078317 A1 | 4/2003 | Lin et al. |
| 2003/0121450 A1 | 7/2003 | Lin et al. |
| 2003/0167093 A1 | 9/2003 | Xu et al. |
| 2003/0216777 A1 | 11/2003 | Tien et al. |
| 2004/0003757 A1 | 1/2004 | Lin et al. |
| 2004/0022825 A1 | 2/2004 | Lagow |
| 2004/0031420 A1 | 2/2004 | Lin et al. |
| 2004/0076685 A1 | 4/2004 | Tas |
| 2004/0137032 A1 | 7/2004 | Wang |
| 2004/0175320 A1 | 9/2004 | Lin et al. |
| 2004/0180091 A1 | 9/2004 | Lin |
| 2004/0185181 A1 | 9/2004 | Matsumoto |
| 2004/0186481 A1 | 9/2004 | Lin et al. |
| 2005/0008759 A1 | 1/2005 | Nie et al. |
| 2005/0076813 A1 | 4/2005 | Lin et al. |
| 2005/0101964 A1 | 5/2005 | Lin et al. |
| 2005/0184417 A1 | 8/2005 | Lin et al. |
| 2005/0186354 A1 | 8/2005 | Lin et al. |

* cited by examiner

METHOD OF INCREASING WORKING TIME OF TETRACALCIUM PHOSPHATE CEMENT PASTE

RELATED APPLICATIONS

The present application is a continuation-in-part application of U.S. patent application Ser. No. 10/773,701, filed Feb. 6, 2004, which is a continuation-in-part application of U.S. patent application Ser. No. 10/607,023, filed Jun. 27, 2003, now U.S. Pat. No. 6,960,249 which is a continuation-in-part application of U.S. patent application Ser. No. 10/414,582, filed Apr. 16, 2003, now U.S. Pat. No. 7,094,282 which is a continuation-in-part application of U.S. patent application Ser. No. 09/615,384, filed Jul. 13, 2000, now abandoned, which is a continuation-in-part of Ser. No. 09/351,912, filed Jul. 14, 1999, now U.S. Pat. No. 6,379,453. The entire contents of the above-listed applications, which are commonly assigned with the present invention, are incorporated herein by reference.

FIELD OF THE INVENTION

The present invention relates to a tetracalcium phosphate (TTCP) for producing fast-setting, bioresorbable calcium phosphate cements (CPC), and in particular, to a tetracalcium phosphate (TTCP) having whiskers on the surface thereof for producing fast-setting, bioresorbable CPC having a high initial strength.

BACKGROUND OF THE INVENTION

In our earlier U.S. Pat. No. 6,648,960 B1, "Method of shortening a working and setting time of a CPC paste," a heat-treatment method to effectively shorten working/setting time of TTCP/DCPA-based CPC paste was disclosed. Without such treatment, the working/setting time of this TTCP/DCPA-based CPC paste would be inconveniently long.

Continued study led to further development of a monolithic TTCP-based CPC with nano-sized whiskers grown on its surface, which composition demonstrates excellent mechanical properties and biological responses and bioresorption behavior. This newly-developed monolithic TTCP cement, however, displays a working/setting time that is too short for certain surgical applications, such as the rather complicated orthopedic and spinal surgeries.

SUMMARY OF THE INVENTION

The present invention discloses a method for significantly increasing working/setting time of the aforesaid TTCP cement. Furthermore, under certain conditions this method can also increase the compressive strength of the cement.

The method for increasing working time of monolithic tetracalcium phosphate (TTCP) cement paste formed by mixing a TTCP powder with an aqueous solution according to the present invention comprises heating said TTCP powder, prior to said mixing, so that said TTCP powder is maintained at a temperature of 50-350° C. for a period of time which is greater than one minute, so that that a TTCP cement paste formed by mixing the resulting heated TTCP powder with said aqueous solution has a prolonged working time in comparison with that formed by mixing TTCP powder that has not been subjected to said heating with said aqueous solution.

DETAILED DESCRIPTION OF THE INVENTION

The present invention discloses a method for preparing a monolithic tetracalcium phosphate (TTCP) cement paste having a prolonged working time, which comprises heating a TTCP powder at a temperature of from 50-350° C. for a period of time which is greater than one minute, and then mixing the heated TTCP powder with an aqueous solution to form a TTCP cement paste, said paste having a prolonged working time in comparison with a TTCP cement paste formed by mixing TTCP powder that has not been subjected to such heating prior to mixing with the aqueous solution.

Preferably, said temperature is 100-300° C., and said period of time is greater than 15 minutes. More preferably, said temperature is 150-250° C., and said period of time is 30 to 120 minutes. The heating of the TTCP powder can be conducted under conditions selected from in air, in vacuum, and in an inert atmosphere.

A suitable TTCP powder for use in the method of the present invention has particle sizes ranging from 0.05 to 100 microns, preferably 0.5 to 50 microns, and particles of said TTCP powder have whiskers on their surfaces having a width ranging from 1 to 200 nm, preferably 1 to 100 nm, and a length ranging from 1 to 2000 nm, preferably 1 to 1000 nm. Said calcium phosphate whiskers preferably have a non-stoichiometric chemical composition, more preferably said calcium phosphate whiskers have a Ca/P molar ratio from about 1.35 to about 4.0, and most preferably from about 1.5 to about 2.5. Said calcium phosphate whiskers generally comprise TTCP as a major phase, and are substantially free of a hydroxyapatite phase.

A suitable process for preparing the TTCP powder having whiskers on the surfaces of the particle thereof comprises:
a) mixing a TTCP powder with a whisker-inducing solution so that basic calcium phosphate whiskers start to grow on surfaces of TTCP particles of said TTCP powder; and
b) terminating the growth of said calcium phosphate whiskers by drying the whisker-inducing solution in the mixture, so that said calcium phosphate whiskers have a width ranging from 1 to 200 nm and a length ranging from 1 to 2000 nm.

Further details of the process can be found in U.S. patent application Ser. No. 10/773,701, filed Feb. 6, 2004, and U.S. patent application Ser. No. 10/607,023, filed Jun. 27, 2003, the disclosures of which are incorporated herein by reference.

The following examples are intended to demonstrate the invention more fully without acting as a limitation upon its scope, since numerous modifications and variations will be apparent to those skilled in this art.

TTCP Preparation

The TTCP powder used in the following examples was fabricated in-house from the reaction of dicalcium pyrophosphate ($Ca_2P_2O_7$) (Sigma Chem. Co., St. Louis, Mo., USA) and calcium carbonate ($CaCO_3$) (Katayama Chem. Co., Tokyo, Japan) by a weight ratio of 1:1.27. The powders were mixed uniformly in ethanol for 12 hours, followed by heating in an oven to let the powders dry. The dried powder mixture was then heated to 1400° C. to allow two powders to react to form TTCP [Brown and Epstein [*Journal of Research of the National Bureau of standards—A Physics and Chemistry* 6 (1965) 69A 12]].

Whisker-inducing Treatment of TTCP Particles $Ca_4(PO_4)_2O$ (TTCP) powder as synthesized was sieved with a #325 mesh. The sieved powder has an average particle size of about 10 μm. An aqueous solution of diammonium hydrogen phosphate was prepared by dissolving 20 mg of diammonium hydrogen phosphate, $(NH_4)_2HPO_4$, in 40 ml deionized water. The resulting solution had a pH value of 8.02. To the TTCP powder the basic aqueous solution of diammonium hydrogen phosphate was added according to the ratio of 1 gm TTCP/13 ml solution. The TTCP powder was immersed in the basic aqueous solution for 10 minutes, filtered rapidly and washed with deionized water, and filtered rapidly with a vacuum pump again. The resulting powder cake was dried in an oven at 50° C. The dried powder was dispersed in ethanol with supersonication. A drop of the dispersion was dripped on a single-side carbon sieve of #325 mesh having a diameter of 3 mm, and left dry to obtain a specimen coated with a thin carbon film for electrical conductivity for TEM examination. A Hitachi Model-HF2000 200 kV field emission transmission electron microscope (TEM) equipped with a Noran Vayager Model 1000 energy dispersive spectroscopy (EDS) system was used for the study. The aperture size for microchemical analysis (Ca/P ratio) is 15 nm.

Whiskers grown on TTCP surface are basic (Ca/P>1.33) in nature. The EDS-determined Ca/P molar ratios are between about 1.4 and 3.8 with an average Ca/P ratio of about 2.1. Majority of whiskers have lengths <300 nm and widths <100 nm.

Heat-treatment Effect on the Working/Setting Time of Whisker-treated TTCP Powder To study the effect of heat treatment on working/setting time and compressive strength, the whisker-treated TTCP powder was heat-treated in an air furnace (N 7/H, Nabertherm®, Germany). Different heat-treatment temperatures (140-400° C.) and times (30 and 120 min) were used for the study. To form a TTCP cement paste, the TTCP powder was mixed with 3M diammonium hydrogenphosphate $((NH_4)_2HPO_4)$ hardening solution with a pH value of 8.6 and liquid/powder ratio of 0.3 ml/gm. After mixing for one minute, the cement paste was uniformly packed in a stainless steel mold under a popularly-used pressure of 0.7 MPa. This mold has an opening of 6 mm in diameter and 12 mm in depth (ASTM F 451-99a) for the preparation of samples for compressive strength testing. At the time of 15 minutes after mixing, the TTCP cement samples were removed from the mold and immersed in 20 ml Hanks' physiological solution (Mears 1977) at 37° C. Since short term (typically within 20-30 minutes after implantation) and long term strengths are both important for TTCP cement (especially for load-bearing applications), the compressive strengths of TTCP cement immersed in Hanks' solution for 20 minutes, 1 day and 7 days were measured.

The working time of the TTCP cement paste was determined as the duration for which the paste was no longer moldable, while setting time was measured according to ISO 1566 standard method. The compressive strength was measured using a desktop mechanical tester (Shimadzu AGS-500D, Tokyo, Japan) at a crosshead speed of 1.0 mm/min.

X-ray diffraction (XRD) was carried out to help identify the phase changes of TTCP cement during immersion. A Rigaku D-MAX B X-ray diffractometer (Tokyo, Japan) with Ni-filtered CuKα radiation operated at 30 kV and 20 mA at a scanning speed of 0.25°/min was used for the study. The various phases were identified by matching each characteristic XRD peak with that compiled in JCPDS files. A Fourier transform infrared spectroscopy (FTIR) system (Jasco, FT/IR-460 Plus, UK) in transmission absorption mode with a spectral resolution of 2 $cm^{-1}$ was used to characterize the various functional groups of the TTCP powder under various heat-treatment conditions.

Results and Discussion

The working/setting time of the present monolithic TTCP-derived CPC can be significantly changed by applying a heat-treatment to the TTCP powder. As can be seen from Table 1, all the investigated heat-treatment conditions caused the working/setting time to become longer than that without heat-treatment. Specifically, when the TTCP powder was heat-treated at a temperature of 300° C. or lower, the working and setting times of the CPC increased respectively from 8 and 9.5 minutes to respectively 12-14 minutes (by 50-75%) and 15-17 minutes (by 60-80%), which are ideal for most applications. When the TTCP powder was heat-treated to 400° C. for 30 minutes, the working and setting times greatly increased to a surgically inconvenient level. When the TTCP powder was heat-treated to 400° C. for 120 minutes, the cement paste was hardly set.

The compressive strength of the TTCP cement can also be modified by heat-treating the TTCP powder. As indicated in Table 2, when the TTCP powder was heat-treated at 140° C. for 30 min, the compressive strengths of CPC immersed in Hanks' solution for 20 minutes and 7 days both largely decreased from 49.2 and 70.5 MPa to 17.5 and 38.8 MPa, respectively, although its 1-day-strength did not change much. When TTCP powder was heat-treated at 200° C. for 30 minutes, both 20 min and 7-day-compressive strengths of CPC significantly increased. Specifically, the CPC derived from such-treated powder had a 7-day-compressive strength (85.1 MPa) higher than that without treatment (70.5 MPa).

When the powder was treated at 200° C. for 120 minutes, the 20-minute and 1-day-compressive strengths further increased to 65.9 and 96.0 MPa (the highest 1-day-strength), respectively. Its 7-day-strength, however, declined to 80.1 MPa. The heat-treatment at 250° C. for 30 minutes is also interesting in that the compressive strength of the TTCP cement continued to increase even after immersion for 7 days. While the heat-treatment at 300° C. for 30 minutes still showed relatively high 1-day and 7-day-strengths, the heat-treatment to 300° C. for 120 minutes or to 400° C. caused the compressive strength of the CPC to largely decline. From a practical point of view, among all heat-treatment conditions investigated in this study, the heat-treatment at about 200-300° C. for about 30-120 min appears to be a suitable range for prolonging the working/setting time, while maintaining (in some cases even increasing) the compressive strength of the monolithic TTCP cement.

TABLE 1

|  | Working time (min) | Setting time (min) |
|---|---|---|
| Non-heat-treated | 8.0 | 9.5 |
| 140° C. 30 min | 12.0 | 15.8 |
| 120 min | 12.3 | 15.3 |
| 200° C. 30 min | 12.5 | 15.8 |
| 120 min | 13.3 | 16.0 |
| 250° C. 30 min | 12.0 | 14.3 |
| 120 min | 12.0 | 14.0 |
| 300° C. 30 min | 12.0 | 15.0 |
| 120 min | 13.8 | 17.3 |
| 400° C. 30 min | 16.5 | 23.0 |
| 120 min | 45.0 | + |

+ cement is hardly set

TABLE 2

| | Compressive strength (MPa) | | |
| --- | --- | --- | --- |
| | 20 min | 1 d | 7 d |
| Non-heat-treated | 49.2 | 90.3 | 70.5 |
| 140° C. 30 min | 17.5 | 86.5 | 38.8 |
| 120 min | 18.0 | 72.6 | 69.6 |
| 200° C. 30 min | 44.9 | 85.2 | 85.1 |
| 120 min | 65.9 | 96.0 | 80.1 |
| 250° C. 30 min | 41.7 | 66.7 | 86.5 |
| 120 min | 42.8 | 88.6 | 58.5 |
| 300° C. 30 min | 29.7 | 91.1 | 80.4 |
| 120 min | 25.6 | 52.3 | 54.3 |
| 400° C. 30 min | 16.1 | 28.5 | 36.2 |

To further understand the effect of heat treatment, XRD was performed on all heat-treated TTCP powders. The XRD pattern of non-heat-treated TTCP powder showed a typical TTCP crystal structure, except the heat-treatment conditions of 300° C./120 minutes and 400° C., the XRD patterns of all heat-treated TTCP powders remained essentially the same as that of non-heat-treated powder. When the TTCP powder was heat-treated to 300° C. for 120 minutes or to 400° C. for 30 minutes, apatite peaks were observed, indicating that a phase transition from TTCP to apatite had occurred under such heat treatment conditions. When the powder was treated to 400° C. for 120 minutes, apatite became the dominant phase.

The formation of apatite under these heat-treatment conditions was reconfirmed by the presence of OH band at 3570 $cm^{-1}$ in FTIR spectra.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method for increasing working time of monolithic tetracalcium phosphate (TTCP) cement paste formed by mixing a TTCP powder with an aqueous solution, said method comprising heating said TTCP powder, prior to said mixing, so that said TTCP powder is maintained at a temperature of 50-350° C. for a period of time which is greater than one minute, and that a TTCP cement paste formed by mixing the resulting heated TTCP powder with said aqueous solution has a prolonged working time in comparison with that formed by mixing TTCP powder that has not been subjected to said heating with said aqueous solution.

2. The method according to claim 1, wherein said temperature is 100-300° C., and said period of time is greater than 15 minutes.

3. The method according to claim 1, wherein said temperature is 150-250° C., and said period of time is 30 to 120 minutes.

4. The method according to claim 1, wherein said heating is conducted in air, in vacuum, or in an inert atmosphere.

5. The method according to claim 1, wherein said TTCP powder has particle sizes ranging from 0.05 to 100 microns, and particles of said TTCP powder have whiskers on their surfaces having a width ranging from 1 to 200 nm and a length ranging from 1 to 2000 nm.

6. The method according to claim 5, wherein said TTCP powder has particle sizes ranging from 0.5 to 50 microns.

7. The method according to claim 6, wherein particles of said TTCP powder have whiskers on their surfaces having a width ranging from 1 to 100 nm and a length ranging from 1 to 1000 nm.

8. The method according to claim 5, wherein said calcium phosphate whiskers have a non-stoichiometric chemical composition.

9. The method according to claim 8, wherein said calcium phosphate whiskers have a Ca/P molar ratio from about 1.35 to about 4.0.

10. The method according to claim 9, wherein said calcium phosphate whiskers have an average Ca/P molar ratio from about 1.5 to about 2.5.

11. The method according to claim 10, wherein said calcium phosphate whiskers comprise TTCP as a major phase.

12. The method according to claim 11, wherein said calcium phosphate whiskers are substantially free of a hydroxyapatite phase.

13. A method for preparing a monolithic tetracalcium phosphate (TTCP) cement paste which comprises heating a TTCP powder at a temperature of from 50-350° C. for a period of time which is greater than one minute, and then mixing the heated TTCP powder with an aqueous solution to form a TTCP cement paste, said paste having a prolonged working time in comparison with a TTCP cement paste formed by mixing TTCP powder that has not been subjected to the heating prior to mixing with the aqueous solution.

14. The method according to claim 13, wherein said temperature is 100-300° C., and said period of time is greater than 15 minutes.

15. The method according to claim 13, wherein said temperature is 150-250° C., and said period of time is 30 to 120 minutes.

16. The method according to claim 13, wherein said heating is conducted in air, in vacuum or in an inert atmosphere.

17. The method according to claim 13, wherein said TTCP powder has particle sizes ranging from 0.05 to 100 microns, and particles of said TTCP powder have whiskers on their surfaces having a width ranging from 1 to 200 nm and a length ranging from 1 to 2000 nm.

18. The method according to claim 17, wherein said TTCP powder has particle sizes ranging from 0.5 to 50 microns.

19. The method according to claim 18, wherein particles of said TTCP powder have whiskers on their surfaces having a width ranging from 1 to 100 nm and a length ranging from 1 to 1000 nm.

20. The method according to claim 17, wherein said calcium phosphate whiskers have a non-stoichiometric chemical composition.

21. The method according to claim 20, wherein said calcium phosphate whiskers have a Ca/P molar ratio from about 1.35 to about 4.0.

22. The method according to claim 21, wherein said calcium phosphate whiskers have an average Ca/P molar ratio from about 1.5 to about 2.5.

23. The method according to claim 22, wherein said calcium phosphate whiskers comprise TTCP as a major phase.

24. The method according to claim 22, wherein said calcium phosphate whiskers are substantially free of a hydroxyapatite phase.

25. The method according to claim 17 further comprising, prior to said heating, a) mixing a TTCP powder with a whisker-inducing solution so that basic calcium phosphate whiskers start to grow on surfaces of TTCP particles of said TTCP powder; and b) terminating the growth of said calcium phosphate whiskers by drying the whisker-inducing solution in the mixture, so that said calcium phosphate whiskers have a width ranging from 1 to 200 nm and a length ranging from 1 to 2000 nm.

* * * * *